United States Patent [19]

Sakurai et al.

[11] Patent Number: 4,514,277
[45] Date of Patent: Apr. 30, 1985

[54] OXYGEN SENSOR ELEMENT

[75] Inventors: Shigenori Sakurai; Takashi Kamo; Toshinobu Furutani; Shirou Kimura; Yoshio Torisu, all of Toyota; Mari Okazaki, Chiryu, all of Japan

[73] Assignee: Toyota Jidosha Kabushiki Kaisha, Toyota, Japan

[21] Appl. No.: 429,458

[22] Filed: Sep. 30, 1982

[30] Foreign Application Priority Data

Dec. 24, 1981 [JP] Japan ................................ 56-210311

[51] Int. Cl.³ ............................................. G01N 27/58
[52] U.S. Cl. ...................................... 204/424; 204/421
[58] Field of Search ............... 204/421, 424, 425, 426; 427/125, 376.3, 376.6, 383.5

[56] References Cited

U.S. PATENT DOCUMENTS

| 4,052,286 | 10/1977 | Gray et al. | 204/125 X |
| 4,098,949 | 7/1978 | Kosiorek | 427/125 X |
| 4,113,896 | 9/1978 | Keiner et al. | 427/125 X |
| 4,121,988 | 10/1978 | Sano et al. | 204/426 X |
| 4,170,530 | 10/1979 | Watanabe et al. | 204/426 |
| 4,280,890 | 7/1981 | Friese et al. | 427/125 X |
| 4,289,802 | 9/1981 | Micheli | 204/421 X |
| 4,294,668 | 10/1981 | Young | 204/424 X |
| 4,296,148 | 10/1981 | Friese | 204/426 X |
| 4,298,573 | 11/1981 | Fujishiro | 204/426 X |
| 4,419,213 | 12/1983 | Oshima et al. | 204/426 X |

Primary Examiner—Howard S. Williams
Assistant Examiner—Nam X. Nguyen
Attorney, Agent, or Firm—Oblon, Fisher, Spivak, McClelland & Maier

[57] ABSTRACT

An oxygen sensor element having an oxygen ion-permeable solid electrolyte having a tabular or columnar shape and electrode layers formed on the solid electrolyte. At least one of the electrode layers is composed of a fired body having a uniform structure consisting of 100 weight parts of a metal and 0.1 to 10 weight parts of a glass which consists of the following materials in molar amounts: $SiO_2$, 62–75%; $ZrO_2$, 7–11%; $R_2O$, 13–23%; $R'O$, 1–10%; $Al_2O_3$, 0–4%; $B_2O_3$, 0–6%; $Fe_2O_3$, 0–5%; $CaF_2$, 0–2%; and $TiO_2$, 0–4%; wherein $R_2O$ is $Na_2O$ which is substantially pure or is substituted by $Li_2O$ within 2 mole percent thereof, and $R'O$ is an oxide selected from the group consisting of the alkaline-earth metal oxides, ZnO and MnO. Disclosed also is a method of producing the oxygen sensor element.

2 Claims, 8 Drawing Figures

OXYGEN SENSOR ELEMENT

BACKGROUND OF THE INVENTION

1. Field of the Invention

The present invention relates to an oxygen sensor element making use of a solid electrolyte, suitable for use in oxygen meter or exhaust gas cleaning system for vehicles.

2. Description of the Prior Art

Oxygen sensor of oxygen concentration cell type, making use of a zirconia solid electrolyte, is known as an oxygen sensor for measuring the oxygen concentration in a gas. In this type of oxygen sensor, however, it is difficult to measure the oxygen concentration in the object gas because of an extremely small electromotive force, when the difference of oxygen concentration between the reference gas and the object gas is small. In addition, the construction of the apparatus becomes complicated because of necessity for the reference gas.

Contrary to the principle of the above oxygen concentration cell, it is known that, when a voltage is applied between electrodes formed on both surfaces of the solid electrolyte, oxygen permeates through the solid electrolyte from one side (cathode side) to the other side (anode side). Therefore, if a part of the surface of one of the electrodes is closed, the rate of permeation of oxygen is decreased correspondingly in response to the closing degree even though the voltage applied thereto is maintained constant, so that the amount of the electric current between two electrodes is decreased. To the contrary, if the area of closing of one electrode surface is maintained constant, the electric current is changed in accordance with the change in the oxygen concentration. A method has been developed for measuring the oxygen concentration through detecting the change in the electric current. An oxygen sensor called "limit current type oxygen sensor" has been known already as an oxygen sensor relying upon the above-explained theory.

The oxygen sensor element of the kind described has an oxygen ion-permeable sintered body having a tabular, disk-like, cylindrical or columnar shape and electrodes formed on both sides of the sintered body and adapted to receive voltage through leads connected thereto. Porous coating layers are formed on the electrode surfaces by flame spray of a spinel type material such as $MgO.Al_2O_3$ to restrict the permeation of oxygen. Since the oxygen permeability of the coating layer largely depends on the diameter of the porosity of the coating layer, and density of the the coating layer, as well as the thickness of the coating layer, the unevenness of thickness of the coating layer formed by the flame spray adversely affects the oxygen permeability to unstabilize electric characteristics of the element. In addition, durability is not so high because the coating layers formed by flame spray tend to peel off during long use.

Furthermore, the step of formation of the electrode is quite complicated and laborious, as will be understood from the following description. Namely, FIG. 4 shows the step of formation of the electrodes, as well as the coating layers. In this step, a sintered body of solid electrolyte is activated and chemical plating is effected on the sintered body. Then, using the chemical plating layers as electrodes, an electroplating is effected to form complete electrodes. Finally, the spinel type material is flame-sprayed onto the electrode.

The restriction of permeation of oxygen may be made by another method called "diffusion hole method" in which a casing having apertures of a predetermined size is placed on the element. This method, however, is quite complicated and impractical.

SUMMARY OF THE INVENTION

Accordingly, an object of the invention is to provide an oxygen sensor element having an electrode layer which serves also as a coating layer for controlling the permeation of oxygen.

Another object of the invention is to provide an oxygen sensor element having a simple construction and free of fluctuation of quality attributable to the difficulty in the management of the production condition.

A further object of the invention is to provide an oxygen sensor element having stable electric characteristics and high durability.

A still further object of the invention is to provide a method of producing oxygen sensor element which makes it possible to produce highly reliable oxygen sensor element with a reduced number of production process.

DETAILED DESCRIPTION OF THE INVENTION

Figure 1:
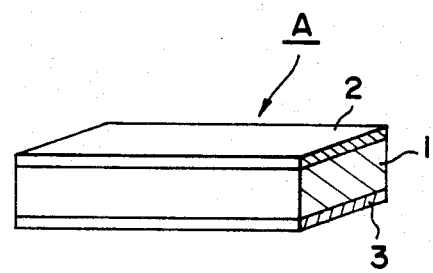
FIG. 1 is a perspective view of an oxygen sensor element in accordance with the present invention.

The oxygen sensor element of the invention is characterized by comprising a tabular or columnar oxygen ion-permeable solid electrolyte and electrode layers formed on both sides of the solid electrolyte and the electrode layers consisting of a fired body composed uniformly containing 100 weight parts of a metal and 0.1 to 10 weight parts of glass.

The method of producing the oxygen sensor element in accordance with the invention is characterized by having the steps of mixing 0.1 to 10 weight parts of glass powder with 100 weight parts of a metal paste, applying the mixture to both sides of a solid electrolyte having a tabular or columnar form and drying and firing the solid electrolyte applied with the mixture.

According to the invention, the solid electrolyte is prepared from an oxygen ion-permeable oxide such as zirconium oxide ($ZrO_2$), titanium oxide ($TiO_2$) or the like containing a stabilizer such as yttrium oxide ($Y_2O_3$), ytterbium oxide ($Yb_2O_3$) in the form of a solid solution. The metallic powder as the material of the electrode layers is selected from a group consisting of materials such as platinum (Pt), rhodium (Rh), palladium (Pd), silver (Ag) which have good heat and oxidation resistances, as well as high electric conductivity, and capable of unstable compounds through reaction with oxygen to make emission of oxygen ion. The glass powder, which exhibits a high resistance to heat, improves the affinity between the solid electrolyte and the metallic powders to refine the electrode layers thereby to restrict the permeation of oxygen. The ratio of the glass powder to be used to the metallic powder is usually selected to range between 0.1 and 10 weight parts, preferably between 0.3 and 2.0 weight parts and more preferably between 0.7 and 1.0 weight parts. The thickness of the electrode layer formed by the uniform mixture of the metallic powder and the glass powder is selected to meet the demand and, hence, can be varied as desired. The electrode thickness, however, is selected usually to be less than 50 $\mu m$, preferably 1 to 40 $\mu m$ and more preferably between 2 and 30 $\mu m$. It is not always necessary that both electrodes layers are the electrode layers of the invention. Namely, in some cases, the electrode formed on one side of the solid electrolyte is the conventional electrode, i.e. an electrode consisting solely of a metal, while the electrode on the other side is formed in accordance with the invention mixing glass powder with metal powder.

The material of the glass powder to be mixed with the metallic powder can have a wide selection and an ordinary heat-resistant glass can fairly be used, although the use of the following materials is preferred.

As glass material, it is desirable to use reinforcing glass fiber for cement since they have alkali-proof property. With respect to these glass materials, their compositions are shown in, for example, Japanese Patent Publication No. 40126/1974 (corresponding to British Patent Application No. 37862/1969) and Japanese Patent Laid-Open No. 54118/1973 (corresponding to British Patent Application No. 51177/1971).

The composition contains, in proportion of mol %,

| | |
|---|---|
| $SiO_2$ | 62~75% |
| $ZrO_2$ | 7~11% |
| $R_2O$ | 13~23% |
| $R'O$ | 1~10% |
| $Al_2O_3$ | 0~4% |
| $B_2O_3$ | 0~6% |
| $Fe_2O_3$ | 0~5% |
| $CaF_2$ | 0~2% |
| $TiO_2$ | 0~4%, | in which $R_2O$ represents $Na_2O$ which can be substituted by $Li_2O$ up to 2 mol % of $R_2O$ and $R'O$ represents oxide selected from a group of alkaline earth metal oxide, zinc oxide and manganese monoxide.

More specifically, a reinforcing glass fiber for cement made by Asahi Fiber Glass Co. can be used in the present invention. The composition thereof is:

| | |
|---|---|
| $SiO_2$ | 62.7% |
| $Na_2O$ | 14.7% |
| $CaO$ | 5.4% |
| $ZrO_2$ | 16.6% |
| $Al_2O_3$ | 0.53% |

It is considered that glass in a metallic paste is melted by heating and it applies the metal to zirconia.

The mixture of the metallic powder and the glass powder is blended together with a suitable organic solvent such as butyl carbitol into the form of a paste. If necessary, it is possible to use an extinguishable organic binder which is harmless in view of process and the performance the product. The paste of the mixture applied to the shaped solid electrolyte is dried and then fired. The firing temperature varies depending on the kinds of the metallic powder and the glass powder but generally ranges between 800° and 1,200° C., preferably between 800° and 1,000° C. and more preferably between 830° and 900° C. The firing time is selected to fall within the range of between 5 and 60 minutes.

The particle size of the metallic powder used as the material of the metallic paste is not limited but is preferably small. For instance, metallic powder of a particle diameter (or mesh) ranging between 5 and 20 $\mu m$ is used as the material.

The particle diameter of the glass powder is selected in accordance with the amount of restriction of oxygen, but generally ranges between 5 and 20 $\mu m$, preferably 5 and 15 $\mu m$ and more preferably 5 and 10 $\mu m$.

A preferred embodiment of the invention will be described hereinunder with reference to the drawings.

Figure 2:
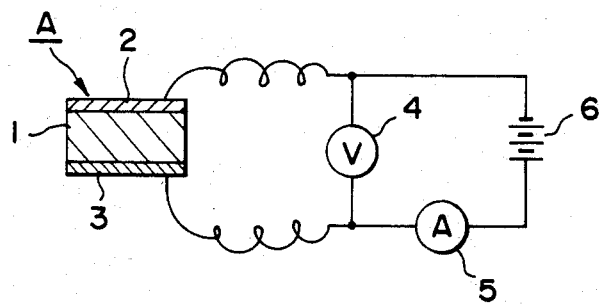
FIG. 2 is a circuit diagram of a circuit for measuring the V-I characteristics.

Referring first to FIG. 1, an oxygen sensor element A in accordance with the invention has a tabular solid electrolyte (oxygen ion-permeable body) 1 on both sides of which formed are heat-resistant electrode layers 2 and 3. FIG. 2 shows an electric circuit of a device for measuring the V-I characteristics of the element in accordance with the invention. An electric circuit is constituted by leads through which the electrode layers of the element A are connected to a power supply 6 and a volt meter 4 and an ammeter 5 connected as illustrated.

Figure 3:
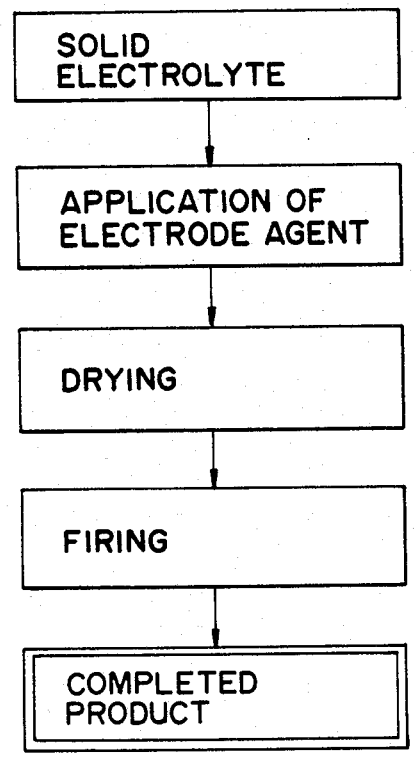
FIG. 3 is an illustration of a production method in accordance with the present invention.
Figure 4:
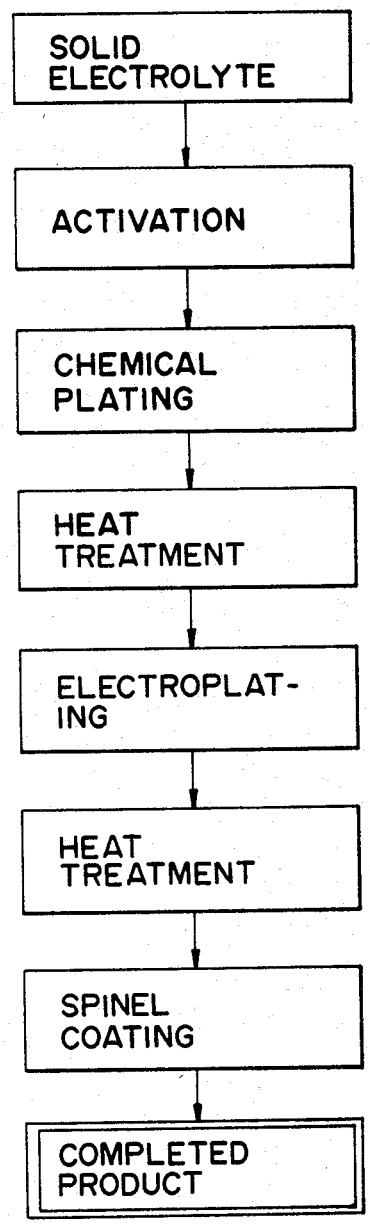
FIG. 4 is an illustration of a conventional production process employing electrode coating step.

FIG. 3 shows the process in accordance with the invention. A mixture of metallic paste and glass powder is directly applied to the opposite surfaces of a solid electrolyte which is already fired, to a thickness of 5 to 500 $\mu m$. Then, after drying at 150° C., the electrode layers are fired at 800° to 1000° C. so that the thicknesses of the electrode layers are reduced to 2 to 30 $\mu m$. The gas permeability is ruled by the thicknesses of the electrode layers and the porosities of the same, provided that the voltage applied thereto is constant.

As will be understood from the foregoing description, the permeation of oxygen is controlled by the electrodes themselves in the oxygen sensor element of the invention, so that the construction is simplified and the production is facilitated as compared with the conventional sensor element which is produced in two stages, i.e. by first forming the electrodes and then covering the electrodes by porous coating layers.

The invention will be more fully understood from the following description of example.

EXAMPLE

Powder of zirconium oxide ($ZrO_2$) of 99.9% purity and powder of yttrium oxide ($Y_2O_3$) of 99.9% purity were used as the material of the solid electrolyte. The powders were picked up at a ratio of 9:1 and were milled and mixed with each other for 5 hours in a wet type ball mill, and were dried at 150° C. for 6 hours. The mixture powder was then calcined at 1200° C. for 4 hours and, after a crushing for 5 hours in a wet type ball mill, and was then dried again for 6 hours at 150° C. The powder thus obtained was then compacted at a pressure of 1200 Kg/cm² into a tabular form of 1 mm thick, 10 mm long and 10 mm wide, and this compacted tabular body was fired for 3 hours in the air at 1800° C. to become a sintered body.

Subsequently, a coating material was prepared from platinum powder of a particle diameter of 0.1μ and a solvent such as butyl carbitol and containing 1 weight part of glass powder of particle diameter of 12μ in relation to 100 weight parts of platinum paste having a solid content of 70%. The glass fiber used here is milled one of the afore-mentioned glass fiber which is manufactured by Asahi Glass Fiber Co. The coating material was applied to both sides of the above-mentioned solid electrolyte such that the thickness of the coating layer was 0.02 mm after the firing. The thickness of the coating layer is varied in relation to the mixture ratio of the glass powder and the thickness can be decreased by increasing the glass powder content. The electrodes were formed by a firing conducted in the air at 900° C. for 0.15 hour, after a 0.5-hour drying at 120° C.

Figure 5:
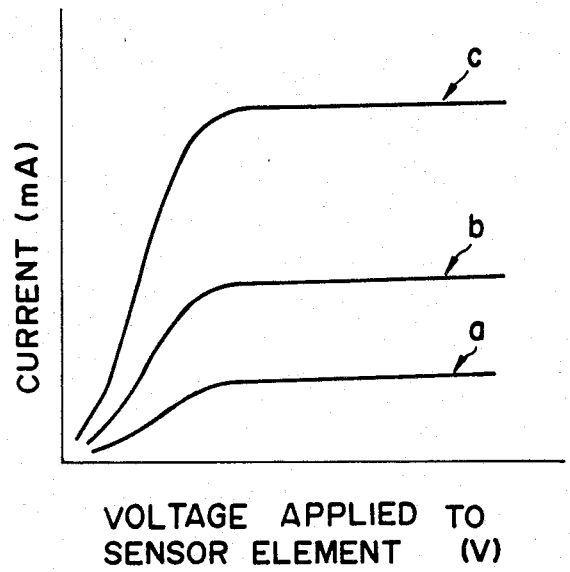
FIG. 5 is a graph showing the V-I characteristics of the element in accordance with the invention.

The oxygen sensor element thus produced was subjected to a test for examining the characteristics to obtain a result as shown in FIG. 5. Namely, the oxygen sensor element was placed in a medium having oxygen concentrations of 2% (curve a), 5% (curve b) and 10% (curve c) while varying the voltages applied thereto, and the electric current generated in the sensor element was measured in relation to the voltage. In each of the curves a, b and c, the flat part substantially parallel to the axis of abscissa represents the limit current corresponding to each oxygen concentration.

Figure 6:
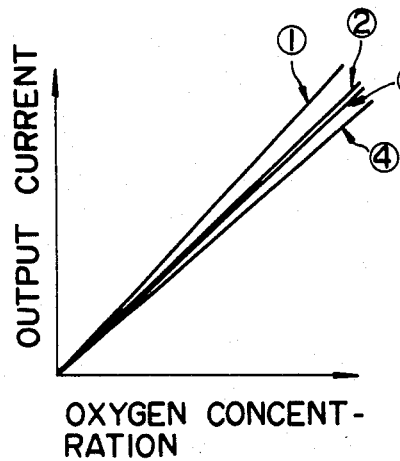
FIG. 6 is a graph showing the output characteristic of an oxygen sensor element of the invention.
Figure 7:
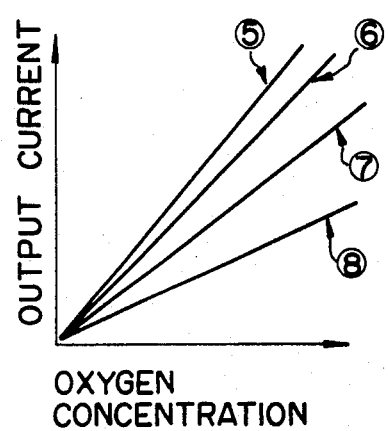
FIG. 7 is a graph showing the output characteristic of an oxygen sensor element of the invention.
Figure 8:
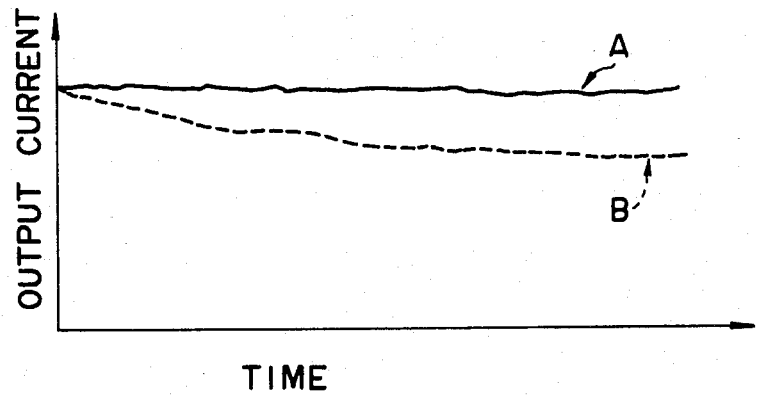
FIG. 8 is a graph showing secular change of the oxygen sensor element A of the invention and a conventional oxygen sensor element B.

FIG. 6 shows the characteristics of four pieces of oxygen sensor elements ①, ②, ③ and ④ produced by the method of the invention, while FIG. 7 shows the characteristics as measured with four pieces of oxygen sensor elements ⑤, ⑥, ⑦ and ⑧ produced by the conventional method. From a comparison between FIGS. 6 and 7, it will be seen that the fluctuation of quality of the product sensor elements of the present invention is smaller than that of the conventional sensor elements. FIG. 8 shows the change with the passage of time of the output current of the sensor element A in accordance with the invention in comparison with that of the conventional sensor element B. It will be realized that the change with the passage of time of the output current is smaller in the element of the invention than in the conventional element.

As has been described, the oxygen sensor element in accordance with the invention is simple in construction and easy to produce as compared with the conventional oxygen sensor element, and can exhibit a stable V-I characteristic while avoiding the fluctuation of the characteristics which is inevitable in the conventional oxygen sensor element due to fluctuation of oxygen diffusion in the coating layer. Furthermore, the change with the passage of time of the output characteristics is very small as compared with the conventional sensor elements. Moreover, the production process is simple and costless to a great advantage from the view point of production and utilization.

What is claimed is:

1. An oxygen sensor element of an oxygen sensor of an oxygen concentration cell comprising an oxygen ion-permeable solid electrolyte shaped in a tabular or columnar shape, with electrode layers formed on both sides of said solid electrolyte, wherein at least one of said electrode layers consists of a uniform fired body containing 100 weight parts of metal powder and 0.1 to 10 weight parts of glass powder consisting of particles having a diameter of 5 to 20 micrometers, and wherein said glass powder consists of reinforcing glass fiber for cement, which consists of the following materials in molar amounts: $SiO_2$, 62-75%; $ZrO_2$, 7-11%; $R_2O$, 13-23%; R'O, 1-10%; $Al_2O_3$, 0-4%; $B_2O_3$, 0-6%; $Fe_2O_3$, 0-5%, $CaF_2$, 0-2%; and $TiO_2$, 0-4%; wherein $R_2O$ is $Na_2O$ which is substantially pure or is substituted by $Li_2O$ within 2 mole percent thereof, and R'O is an oxide selected from the group consisting of the alkaline-earth metal oxides, ZnO and MnO.

2. An oxygen sensor element of an oxygen sensor of an oxygen concentration cell comprising an oxygen ion-permeable solid electrolyte shaped in a tabular or columnar shape, with electrode layers formed on both sides of said solid electrolyte, wherein at least one of said electrode layers consists of a uniform fired body containing 100 weight parts of metal powder and 0.1 to 10 weight parts of glass powder consisting of particles having a diameter of 5 to 20 micrometers, wherein said glass powder consists of reinforcing glass fiber for cement, which consists of the following materials in molar amounts: $SiO_2$, 62.7%; $Na_2O$, 14.7%; CaO, 5.4%; $ZrO_2$, 16.6%; and $Al_2O_3$, 0.53%.

* * * * *